United States Patent [19]

Elia

[11] Patent Number: 5,378,152
[45] Date of Patent: Jan. 3, 1995

[54] METHOD AND APPARATUS FOR INSTALLATION OF DENTAL IMPLANT

[75] Inventor: James P. Elia, Scottsdale, Ariz.

[73] Assignees: Dental Marketing Specialists, Inc., Scottsdale, Ariz.; Jerry W. Bains and Salee C. Bains, Carefree, Ariz.; a part interest

[21] Appl. No.: 877,132

[22] Filed: May 1, 1992

[51] Int. Cl.⁶ .......................... A61C 8/00; A61C 5/00
[52] U.S. Cl. .................................. 433/173; 433/215; 433/175
[58] Field of Search .............. 433/173, 174, 175, 176

[56] References Cited

U.S. PATENT DOCUMENTS

| | | | |
|---|---|---|---|
| 4,531,916 | 7/1985 | Scantlebury et al. | 433/173 |
| 4,552,532 | 11/1985 | Mozsary | 433/174 |
| 4,713,006 | 12/1987 | Hakamatsuka et al. | 433/173 X |
| 4,728,331 | 3/1988 | Russier | 433/175 X |
| 4,872,840 | 10/1989 | Bori | 433/173 |
| 4,957,819 | 9/1990 | Kawahara et al. | 433/173 X |
| 5,002,488 | 3/1991 | Homsy | 433/173 X |

FOREIGN PATENT DOCUMENTS

| | | | |
|---|---|---|---|
| 1075793 | 2/1960 | Germany | 433/173 |
| 2182250 | 7/1990 | Japan | 433/173 |
| 0679119 | 12/1991 | Switzerland | 433/173 |

*Primary Examiner*—Gene Mancene
*Assistant Examiner*—Nicholas D. Lucchesi
*Attorney, Agent, or Firm*—Tod R. Nissle

[57] ABSTRACT

A dental implant shaped like a bottle includes an involute which extends inwardly from the bottom of the implant. The smooth arcuate outer surface of the implant minimizes the likelihood the implant becoming infected after the implant is installed in alveolar bone.

6 Claims, 8 Drawing Sheets

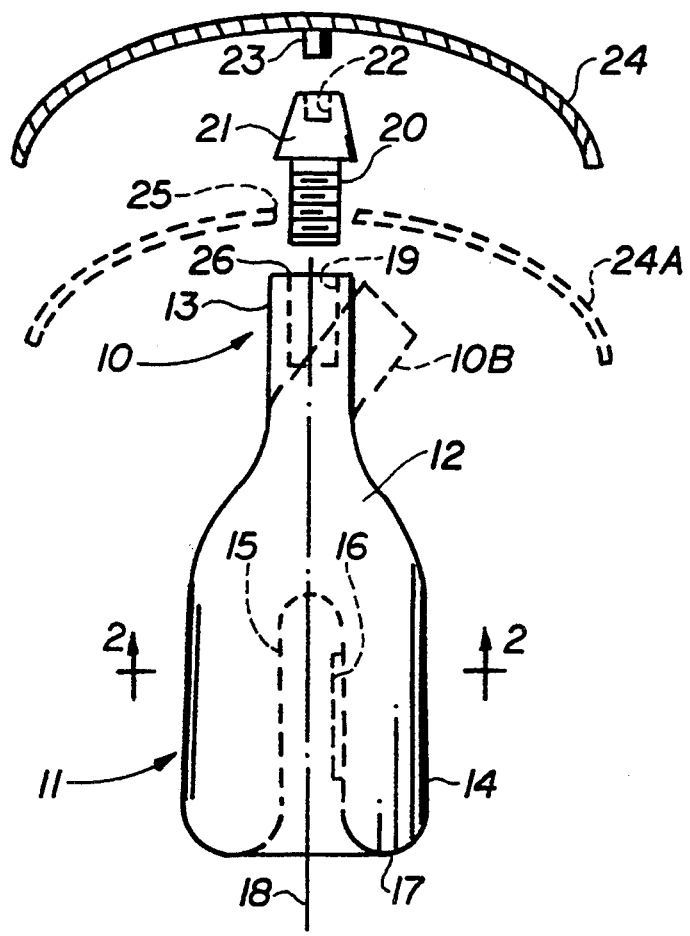
FIG. 1
FIG. 2
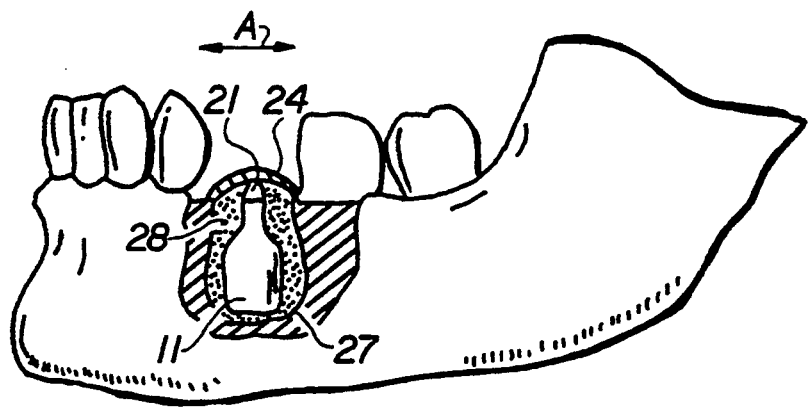
FIG. 3

METHOD AND APPARATUS FOR INSTALLATION OF DENTAL IMPLANT

This invention relates to a method and apparatus for installing a dental implant in the alveolar or basal bone of a patient.

More particularly, the invention relates to a method and apparatus fear a dental implant which reduces the likelihood of the implant becoming infected, which does not require an opening of precise size to be drilled or formed in the alveolar bone to receive the dental implant, which can mount an implant on existing alveolar bone without requiring alteration of the structure of the bone, which prevents the juncture of the dental implant and artificial tooth attached to the implant from being exposed in the event the patient's gums recede, which enables bone mass lost as the patient ages to be replaced, and which enables an implant to be used when drilling an opening in the alveolar bone is precluded due to the existence of a nerve in the bone.

Dental implants are well known in the art. See, for example, U.S. Pat. Nos. 5,006,070 to Komatsu, 4,693,686 to Sendax, 4,812,120 to Flanagan et al., 4,818,559 to Hama et al., 4,671,768 to Ton, and 4,175,565 to Chiarenza et al. Such prior art dental implants and methods for installing the same have disadvantages.

First, the implants normally must be press fit or wedged into an opening formed in the alveolar bone. Force fitting an implant into the alveolar bone is not desirable because it is uncomfortable for the patient, runs the risk of cracking the jaw bone, further damages the bone, and, most importantly, increases the likelihood of infection because dental implants ordinarily are provided with an assortment of ridges, points, or teeth which serve as desirable sites for bacteria, both before and after the implant is inserted in the bone. As a consequence, dental implants typically appear medieval.

Second, force fitting an implant in the alveolar bone requires that the opening formed in the bone have a specific size which roughly conforms to the outer dimensions of the implant so the implant can be force fit into the opening. If a dental surgeon selects a drill of improper size, or waggles the drill while forming the hole in the alveolar bone, the implant may not seat properly in the bone and will work free from the jaw.

Third, the surface area of the portion of the implant imbedded in the jaw is typically reduced because of the common belief that fenestrations of various size must be formed in the implant to permit bone to grow through and anchor the implant.

Fourth, conventional implant procedures often can not be used because the drilling of a opening in the alveolar bone is prohibited by a nerve which passes through the bone.

Fifth, conventional implant procedures also often can not be successfully used when the jaw bone has significantly receded, as can be the case with older patients.

Sixth, conventional implant procedures do not offer a way of replacing alveolar bone which has been lost due to aging or to some other cause resulting in injury to the bone.

Seventh, conventional implant procedures typically do not permit the ready adjustment of the position of the implant after the implant is inserted in the opening formed in the alveolar bone. Correcting the position of an improperly installed implant is often difficult, unless the implant is completely removed from the alveolar bone, which is a time consuming process.

Accordingly, it would be highly desirable to provide an improved dental implant method and apparatus which would not require the force fitting of an implant in the alveolar bone, would not require the formation of a specific size opening in the jaw bone, would provide an implant less likely to loosen after being inserted in the alveolar bone, would permit an implant to be used on alveolar bone housing a nerve, would enable implants to be successfully utilized on alveolar bone which has receded with age, and would permit the position of the implant to be readily adjusted after the implant is inserted in an opening in the alveolar bone.

Therefore, it is a principal object of the invention to provide an improved dental implant method and apparatus.

Another object of the invention is to provide an improved dental implant which can be inserted in an opening in the alveolar bone without requiring that the opening must, within close tolerances, have a specific shape and dimension.

A further object of the invention is to provide an improved dental implant which permits ready adjustment of the position of the implant after the implant is placed in an opening formed in the jawbone.

Still another object of the invention is to provide a dental implant method which permits an implant to be attached to alveolar bone housing a nerve.

Yet a further object of the invention is to provide a dental implant method which allows an implant to be utilized on alveolar bone which has experienced significant loss and recession of its mass.

Another and further object of the instant invention is to provide an improved dental implant which is less likely to loosen after insertion in the alveolar bone.

These and other, further and more specific objects and advantages of the invention will be apparent to those skilled in the art from the following detailed description thereof, taken in conjunction with the drawings, in which:

FIG. 1 is a front view of a dental implant apparatus constructed in accordance with the principles of the invention;

FIG. 2 is a section view of the dental implant apparatus of FIG. 1 illustrating internal construction details thereof;

FIG. 3 is a side view of a portion of the lower jaw bone illustrating the implant of FIG. 1 installed in an opening formed in alveolar bone;

Figure 4:
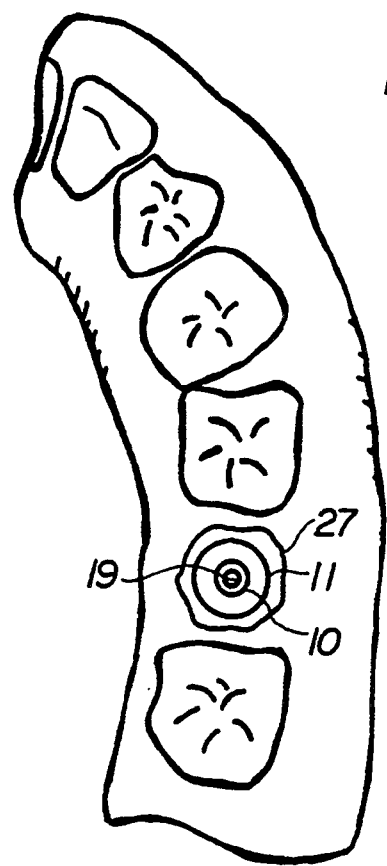
FIG. 4 is a top view of a portion of the jaw bone of FIG. 3 further illustrating the installation of the implant of FIG. 1 therein.
Figure 5:
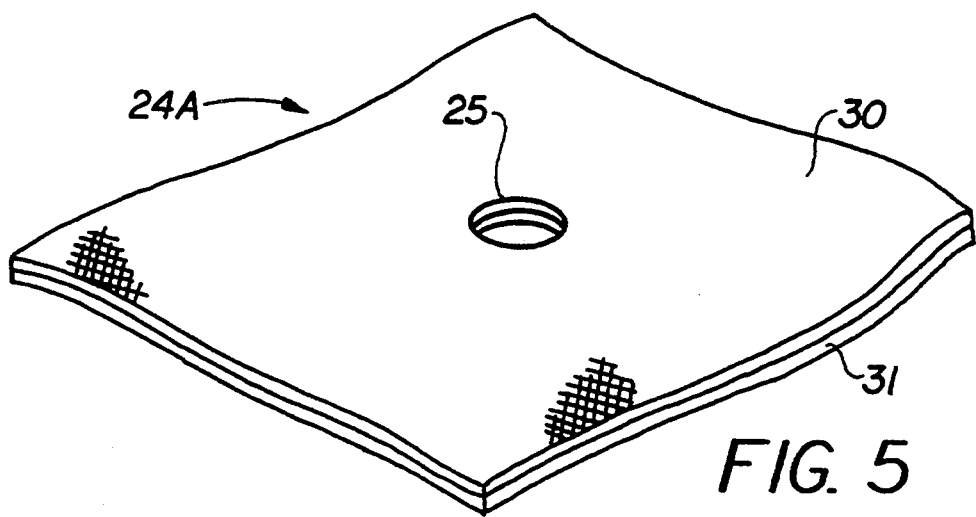
FIG. 5 is a perspective view illustrating a sheet of protective material used to shield hydroxyapatite composition used to pack an implant into an opening in the alveolar bone.

Briefly, in accordance with my invention, I provide an improved dental implant. The implant comprises a body having a closed top and a bottom and a longitudinal axis extending through the top and bottom; and, a head supported on the top of the body and adapted to support an artificial tooth. The body extends downwardly from the top and terminates at a lower end remote from the head. The body includes a smooth continuous surface extending from the top to the bottom and defining the periphery of the top and the bottom. The smooth surface circumscribes the longitudinal axis. The body also includes a hollow centrally defined therein, circumscribed by the continuous and extending into the body through the bottom a selected distance toward the top. The hollow only opens at the lower end of the body. The head can have a smaller width than the body. The hollow can be an involute. The continuous surface can be shaped such that when any cross section of the body is taken perpendicular to the longitudinal axis, each point on the continuous surface is generally equidistant from the longitudinal axis.

In another embodiment of the invention, I provide a method of anchoring a dental implant in the alveolar bone of a patient. The method comprises the steps of forming an opening in the alveolar bone; inserting a dental implant in the opening, the implant comprising a body and a head supported on the body and adapted to support an artificial tooth, the dental implant only partially filling the space in the opening; and, packing the space in the opening which is unoccupied by the dental implant with a hydroxyapatite composition. The opening can be large enough to permit the implant to be readily tilted from side to side after insertion in the opening. After the opening is packed with hydroxyapatite composition, the implant can be adjusted or tilted from side to side and the hydroxyapatite composition then repacked.

In a furthest embodiment of the invention, I provide a dental implant comprising a body; a head supported on the body and having a longitudinal axis and including an upper portion adapted to support an artificial tooth and having a distal tip and a peripheral surface circumscribing the longitudinal axis and extending downwardly from the distal tip toward the body, and, a lower portion supported on the body; and, a healing cap. The healing cap is adapted to be removably attached to the upper portion of the head and includes a prophylactic portion which, when the healing cap is attached to the upper portion, slidably extends downwardly from the tip over and covers at least a portion of the peripheral surface such that when the implant is inserted in an opening in the alveolar bone, a solidified filler composition at least partially fills the opening, extends downwardly from the distal tip toward the body, and covers the prophylactic portion, the lower portion, and the body, and the healing cap is removed from the head, a space exists intermediate the portion of the peripheral surface and the solidified filler composition such that an artificial tooth can extend into the space and cover the distal tip of the head. The filler composition can be a hydroxyapatite composition.

In still another embodiment of the invention, I provide a method of anchoring a dental implant to the alveolar bone of a patient. The method comprises the steps of placing the dental implant at a selected site on the alveolar bone, the dental implant comprising a body and a head supported on the body and adapted to support an artificial tooth; packing a malleable hydroxyapatite composition around the dental implant and against alveolar bone of the patient; and, covering the malleable hydroxyapatite composition with a pliable sheet of material to at least partially prevent gum tissue from growing into the hydroxyapatite composition while the hydroxyapatite composition solidifies.

In yet another embodiment of the invention, I provide a dental implant for a ridge of alveolar bone normally at least partially covered by gum tissue. The implant comprises a body having a top and a pair of opposed feet each extending downwardly from the top to a tip at a lower end remote from the top, the feet having an inner surface shaped, contoured, and dimensioned to conform to the ridge of alveolar bone when the gum tissue is removed from the ridge; and, a head supported on the body and adapted to support an artificial tooth.

In yet still another embodiment of the invention, I provide a method of anchoring a dental implant to the existing alveolar bone of a patient, the bone having an existing outer surface. The method comprises the steps of removing alveolar bone to form an outwardly projecting anchor peg having a selected shape and dimension; and, inserting a dental implant over the anchor peg. The dental implant comprises a body and a head support on the body and adapted to support an artificial tooth. The body extends downwardly from the head to a lower end remote from the head and having an aperture formed in the lower end. The aperture is shaped and dimensioned to be slidably inserted on and conform to the outwardly projecting anchor.

Turning now to the drawings, which depict the presently preferred embodiments of the invention for the purpose of illustrating the practice thereof and not by way of limitation of the scope of the invention and in which like reference characters refer to corresponding elements throughout the several views, FIG. 1 illustrates dental implant apparatus which is constructed in accordance with the principles of the invention and includes a dental implant which has the general shape of a wine bottle and includes a cylindrical head 10 attached to a body 11. The closed top 12 of body 11 has a smooth continuous conical outer surface which tapers from the smooth continuous outer cylindrical surface 14 of the bottom 11 into the smooth cylindrical outer surface 13 of head 10. The conical outer surface of top 12, as do smooth cylindrical surfaces 14 and 13, completely circumscribes longitudinal axis and centerline 18. Head 10 can, if desired, be bent at some selected angle with respect to axis 18 and body 11 as indicated by dashed lines 10B or can be tapered in the manner of head 10A in FIG. 12. The bottom of body 11 extends downwardly from the top 12 and terminates at lower end 17 remote from the head 10. Involute or hollow 15 is formed centrally within body 11, is circumscribed by continuous surface 14, and extends upwardly into body 11 a selected distance toward top 12. Hollow 15 opens only at the lower end 27. Head 13 has a smaller diameter than body 11. An internally threaded aperture 19 is formed in head 13 to receive the externally threaded end 20 of a healing cap. The frustroconical head 21 of the healing cap has a cylindrical aperture 22 formed therein. Cylindrical member 23 is attached to pliable fabric sheet 24 and is shaped to be removably snap fit into aperture 22. The sheet 24 can be secured to the healing cap or head 10 using any convenient means. For example, an aperture 25 can be formed through a pliable sheet 24A and sized such that end 20 slides through aperture 25 and permits sheet 24A to be compressed between head 21 and the circular distal end 26 of head 10. Rib 16 outwardly depends from the smooth cylindrical wall circumscribing and defining hollow 15 and, when hollow 15 is filled with hydroxyapatite or bone in a manner which will be described, prevents the dental implant from rotating about axis 18. Most infection in a tooth begins at the gum line and works its way downwardly toward the root of the tooth. The smooth continuous outer surfaces 13, 14 of the implant of FIG. 1 facilitate determining how far, if at all, infection has penetrated downwardly along the outer surfaces of the implant. The extension of the outer surfaces of the implant from the distal end 26 of the head to the lower end 17 make it difficult for infection to enter hollow 15. In many conventional implants, once infection extends a short distance into the bone, it is a simple matter for the infection to spread laterally under portions of the implant. Consequently, in the implant of FIG. 1 it is important that perforations are not formed through the continuous outer surfaces 13, 14, or the conical surface of top 12. The large area of surfaces 13 and 14 and of the outer conical surface of top 12 help distribute the forces which are produced on an artificial tooth mounted on the implant and decrease the likelihood that the implant will come loose. The smooth curvature and lack of ridges or points extending outwardly from implant surfaces 13 and 14 also decreases the likelihood that stress fractures will be formed in the alveolar bone during the use of an artificial tooth attached to the implant.

The installation of the implant apparatus of FIGS. 1 and 2 in alveolar bone is illustrated in FIGS. 3 and 4. As shown in FIG. 4, an opening 27 is drilled or otherwise formed at a selected location in the alveolar bone and the dental implant is inserted in opening 27. FIG. 4 illustrates opening 27 immediately after the dental implant has been inserted therein. Opening 27 is larger than the dental implant so that the head 10 can be grasped manually or with a dental instrument and tilted from side to side in opening 27. The space between the dental implant and the sides of opening 27 which circumscribe the implant is packed with a malleable hydroxyapatite composition 28. Hollow 15 can also be packed with the hydroxyapatite composition 28 before the implant is inserted in opening 27. After the composition 28 is packed into opening 27 around the dental implant, the head 10 can, if desired, be laterally moved in directions like those indicated by arrows A to tilt and reposition the implant in opening 27. After the dental implant is in the desired position in opening 27, the hydroxyapatite composition is repacked, and member 23 is snapped into aperture 22 in head 21 to position sheet 24 over opening 27 in the manner illustrated in FIG. 3. Sheet 24 can be trimmed as appropriate to cover opening 27. Although not shown in FIG. 4, gum tissue ordinarily at least partially covers and helps maintain sheet 24 in its desired position. Sheet 24 can comprise GORTEX or any other suitable pliable material which helps prevent gum tissue from growing into the hydroxyapatite composition while it solidifies. If desired, sheet 24 can comprise a resorbable material. The GORTEX is left in place for a period of two to twelve months while the surrounding bone grows into and causes the hydroxyapatite composition to solidify and anchor the dental implant in place. After the hydroxyapatite composition has solidified, the healing cap and the sheet 24 are removed such that the gum tissue covers the solidified hydroxyapatite composition- The internally threaded aperture 19 in the head 10 of the implant is used to attach an artificial tooth to the implant.

GORTEX is produced by W. L Gore & Assoc., Inc. Regenerative Technologies of 3773 Kaspar Avenue, Flagstaff, Ariz. 86003-2500, USA. If desired, a pliable sheet 24A can include a layer of GORTEX or similar pliable material laminated with an undercoating of collagen, polyglycolic acid, or another desired material. The collagen imparts a stiffness to sheet 24A and over time is gradually dissolved by the body. GORTEX is an expanded polytetrafluroethylene (e-PTFE) material.

Hydroxyapatite is a crystalline substance containing calcium and phosphorus and is found in certain rocks. It is the basic constituent of bone. The hydroxyapatite composition used to pack opening 27 can simply comprise a dry hydroxyapatite powder. The hydroxyapatite is, however, normally mixed with a liquid substance to form a slurry or more malleable composition which is more readily packed and remains in fixed position than dry hydroxyapatite powder. Hydroxyapatite powder can be mixed with water, plaster, collagen, dextran, epinephrine, or some other desirable material. The hydroxyapatite can be obtained from natural mineral sources, from ground bone, etc. Materials other than hydroxyapatite compositions can be used to fill and pack opening 27. Such other materials can include organic and inorganic matrices and/or combinations thereof. These matrices can be porous, non-porous, active and/or resorbable matrices, or totally inert. For example, coral and coral anlogs, polymethyl methacrylate, polyethylene, PTFE (polytetrafluroethylene), polysufone, polymers, polyethylene glycols, osteomin (bone ash), autogenous bone, freeze dried demineralized bone, resorbable and non-resorbable hydroxyapatite, xenographs (bovine), miniscrews, allografts, composites, polyethylene glycol propionaldehyde, HAPSET, or the patient's own bone can be utilized.

Figure 6:
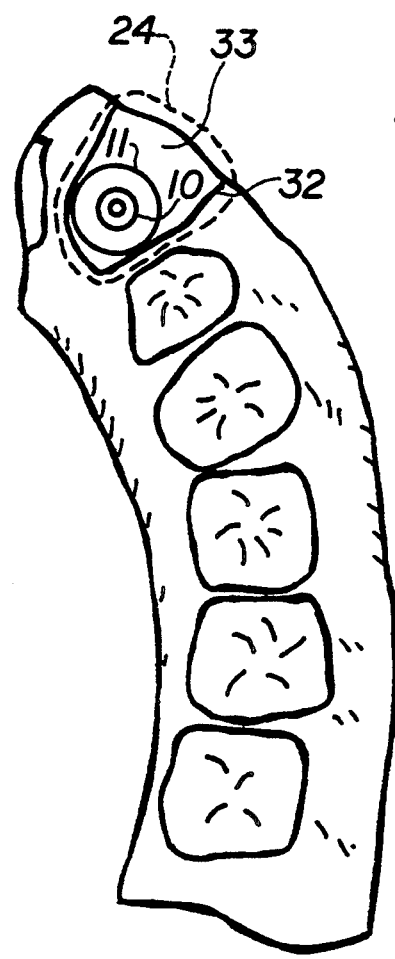
FIG. 6 is a top view of a portion of the lower jaw bone illustrating the insertion of an implant in an opening formed by laterally drilling into the jaw bone.
Figure 7:
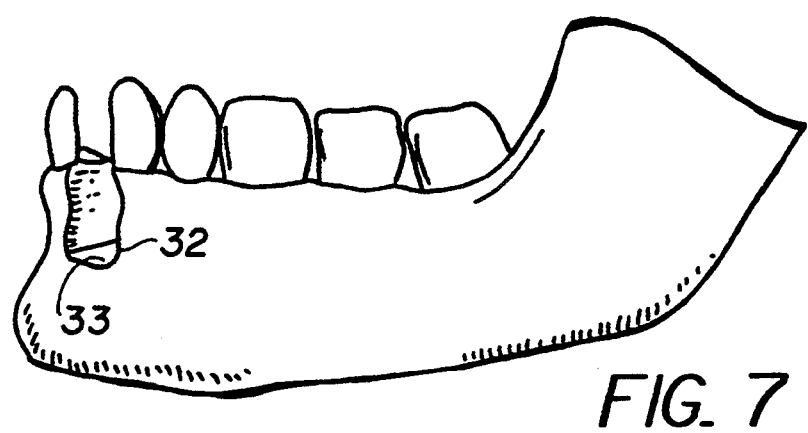
FIG. 7 is a side view of the jaw bone of FIG. 7 further illustrating the lateral opening formed in the jaw bone.

In some cases, it is preferable to produce an opening for a dental implant by forming an aperture in the alveolar bone which opens laterally or outwardly away from the inside of the patient's mouth. Such an outwardly opening aperture 32 is illustrated in FIGS. 6 and 7. In FIG. 7, the dental implant has not yet been inserted on floor 33 of aperture 32. FIG. 6 illustrates the implant in aperture 32. A malleable hydroxyapatite composition is utilized to pack the dental implant in aperture 32. Once aperture 32 is packed with hydroxyapatite composition and the implant is properly positioned in the hydroxyapatite composition and aperture 32, a healing cap is used to attach a pliable layer 24 of material to head 10 to protect the hydroxyapatite composition from invasion by epithelial or other living tissue while the composition hardens. After an appropriate period of time has passed and the bone has grown into and hardened the hydroxyapatite composition, the healing cap and layer of material are removed and an artificial tooth is attached to head 10 using internally threaded aperture 19.

Figure 8:
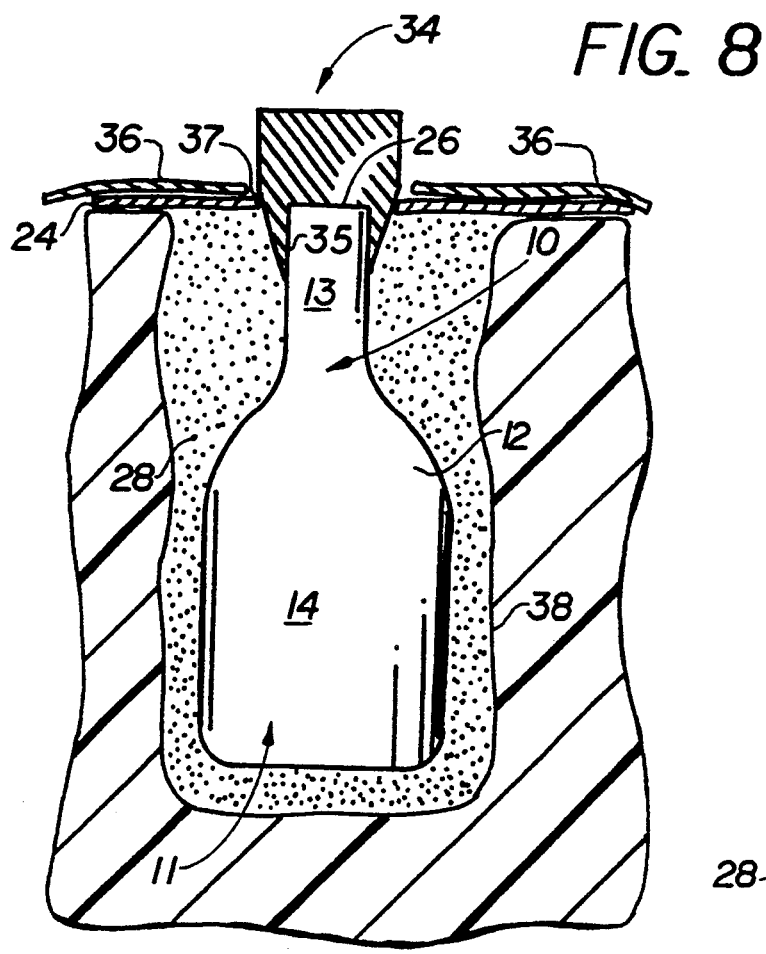
FIG. 8 is a side partial section view illustrating an alternate embodiment of the implant of the invention inserted in an opening formed in the alveolar bone.
Figure 8A:
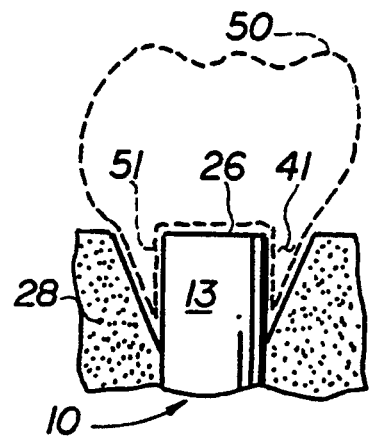
FIG. 8A is a side view illustrating a portion of the implant of FIG. 8 after the healing cap is removed.
Figure 9:
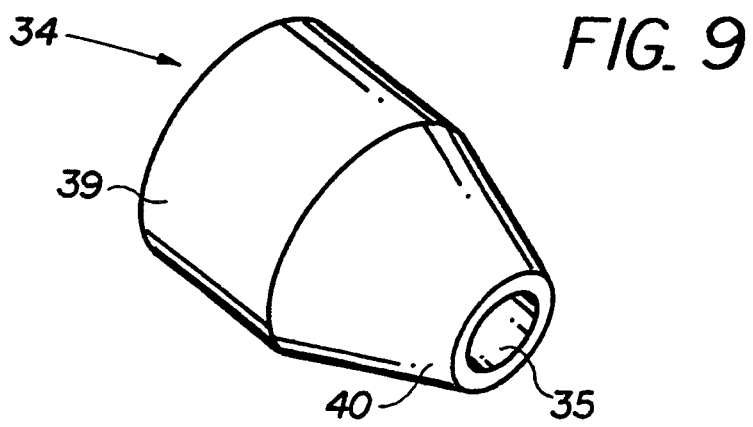
FIG. 9 is a perspective view illustrating a healing cap used in the implant of FIG. 8.

An alternate embodiment of a healing cap 34 is illustrated in FIGS. 8 and 9. Cap 34 includes internal cylindrical aperture 35 shaped to slidably fit over the circular distal end 26 of head 10 and to cover at least a portion of the cylindrical peripheral surface 13 of head 10 of the wine bottle shaped implant of FIG. 1. The pliable sheet 24 in FIG. 8 has a circular aperture 37 formed therethrough which is large enough to slide a selected distance up the conical tip of cap 34, in the manner shown in FIG. 8, but which is too small to slide over the cylindrical upper end 39 of cap 34. Consequently, the conical end 40 of cap 34 functions to hold the sheet 24 in position against the hydroxyapatite composition 28 in the manner illustrated in FIG. 8. Further, a portion of the conical end 40 of cap 34 extends downwardly along surface 13 and past end 26 so that after the composition 28 has solidified and cap 34 is removed from head 10, a conically shaped space 41 (FIG. 8A) exists intermediate the solidified composition 28 and the upper portion of surface 13. When an artificial tooth 50 is subsequently attached to head 10 using the internally threaded aperture 19 formed therein, the lower portion of tooth 50 can include a cylindrical aperture 51 which slides over the upper end of head 10 and covers distal end 26. As would be appreciated by those of skill in the art, either sample implants or impression analogs of the head 10, 10A (FIG. 12) of the support member 70 (FIG. 12) of each implant can be provided to a dental laboratory so that the lower margins of an artificial tooth 50 can be perfectly sized to extend into and completely fill the conically shaped space 41. Distal end 26 ordinarily is positioned at the gum line after the implant is inserted in an opening 38 formed in the alveolar bone. Accordingly, the portions of the artificial tooth 50 extending into space 41 extend below the gum line of the patient.

Figures 10A, 10B, 10C:
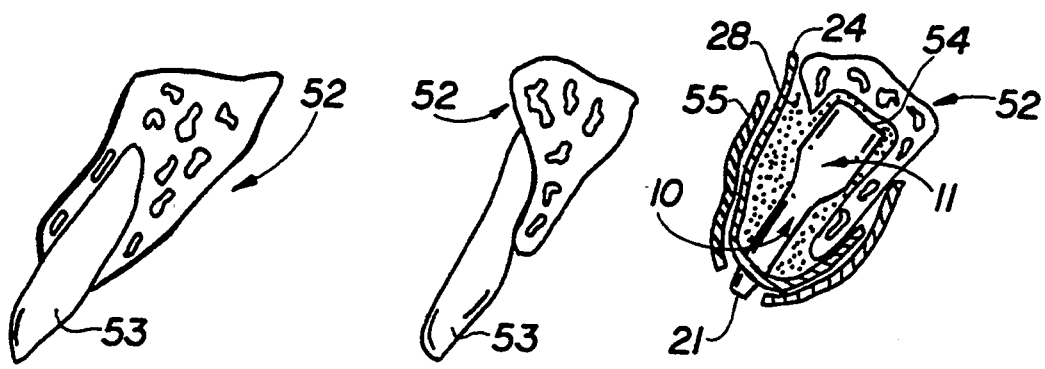
FIG. 10A is a side section view illustrating normal alveolar bone structure around an incisor tooth.
FIG. 10B is a side section view illustrating the recession of the alveolar bone structure from around the incisor tooth of FIG. 10A.
FIG. 10C is a side view illustrating the insertion of an implant in the bone structure of FIG. 10C after the incisor tooth is removed or falls out.

FIG. 10A illustrates a normal, healthy alveolar bone 52 supporting an incisor tooth 53. In FIG. 10B, the bone 52 has receded due to age or other factors. In FIG. 10C, tooth 53 has been removed; a cylindrical aperture 54 has been drilled or otherwise formed in the bone 52; an implant has been inserted in aperture 54; a malleable hydroxyapatite composition 28 has been packed into aperture 54, around the implant, and against the bone 52; a layer of pliable material 24 has been attached to head 10 with the head 21 of a healing cap and extends over the hydroxyapatite composition 28; and, the gum tissue has been positioned over material 24. After the bone 52 grows into the hydroxyapatite composition 28 and the composition 28 solidifies, the healing cap and material 24 are removed, and an artificial tooth is attached to head 10. The hydroxyapatite composition applied to the implant and bone 52 in FIG. 10C is used to augment or build the bone 52 back up to a shape and dimension resembling or duplicating its original normal shape and dimension illustrated in FIG. 10A. A particular advantage of the dental implant methodology of the invention is that it permits hydroxyapatite compositions to be used to augment and enlarge existing alveolar bone structure while at the same time facilitating the anchoring of an implant to alveolar bone. To facilitate the anchoring of an implant in the existing alveolar or basal bone, indents or grooves can be formed in the bone or in the surface of the implant to receive hydroxyapatite or other material used to fill or pack into or around the alveolar or basal bone and the implant.

Figures 10D, 10E, 10F:
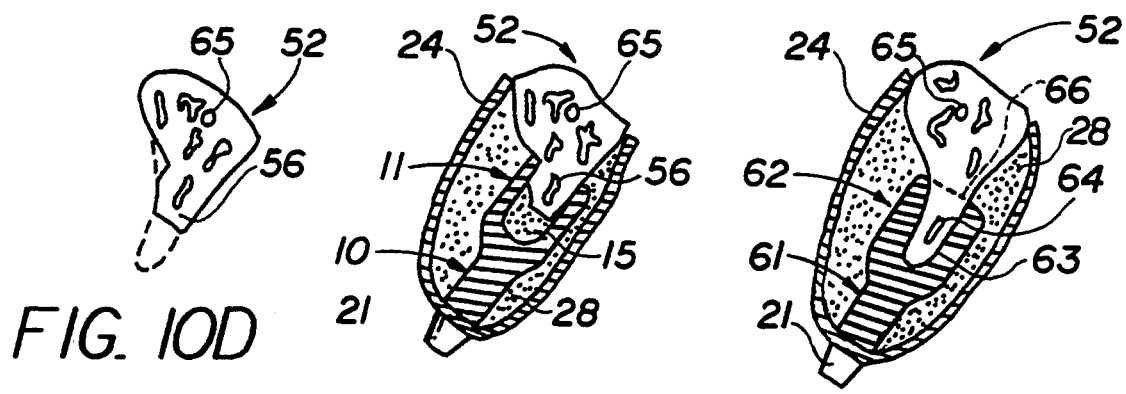
FIG. 10D is a side view illustrating the alveolar bone structure of FIG. 10B after the incisor tooth is removed and a circular drill is used to cut away some of the alveolar bone to form a cylindrical anchor peg.
FIG. 10E is a side partial section view illustrating a dental implant slidably installed on the anchor peg of FIG. 10D and packed with a malleable hydroxyapatite composition.
FIG. 10F is a side partial section view illustrating the alveolar bone structure of 10B after the incisor tooth is removed and an implant is slid onto the existing alveolar bone structure without altering the structure.

In FIG. 10D, the tooth 53 has been removed from the alveolar bone 52 of FIG. 10B and a circular drill has been used to remove some of the bone 52 to form a cylindrical anchor peg 56 which is shaped and dimensioned to be slidably received by the involute 15 of the implant of FIG. 1 in the manner illustrated in FIG. 10E. After involute or hollow 15 is slid onto peg 56, malleable hydroxyapatite composition is packed around the body 11 and head 10 of the implant and the head 21 of the healing cap is used to attach pliable material 24 to head 10. If desired, hydroxyapatite composition 28 can also be inserted in hollow 15 before hollow 15 is slid onto peg 56. One the hydroxyapatite composition has solidified, the healing cap and material 21 are removed, and an artificial tooth is attached to head 10. The bone 52 illustrated in FIGS. 10D and 10E includes a nerve 65.

Figure 11:
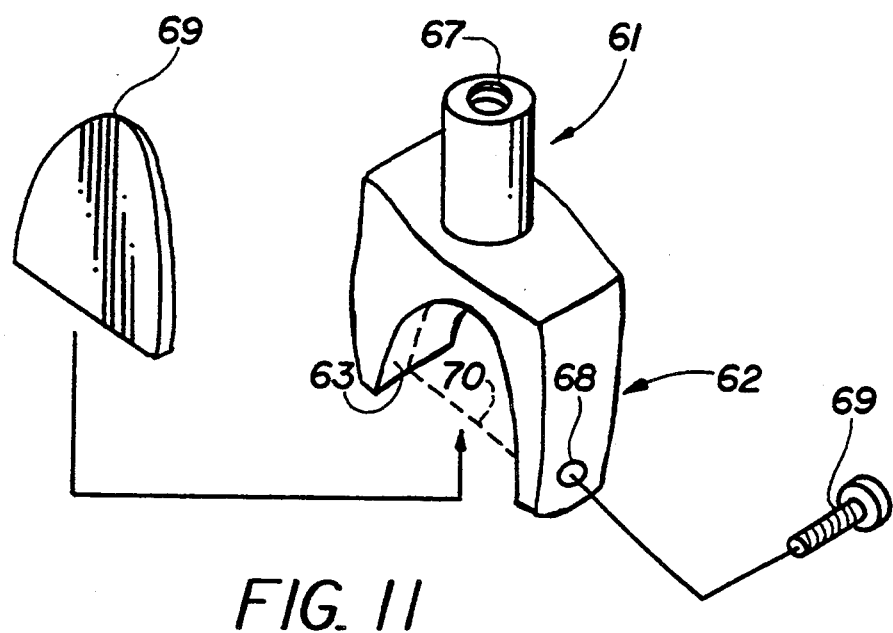
FIG. 11 is a perspective view illustrating an implant of the type which can be fit to an existing alveolar bone structure.

In FIG. 10F, the tooth 53 has been removed from the alveolar bone 52 of FIG. 10B and shape of the ridge 64 of bone 52 has not been altered. An implant has been placed on ridge 64. The implant includes head 61, body 62, and arch or U-shaped aperture 63. Aperture 63 is shaped and dimensioned to conform to and slide on to ridge 64 in the manner illustrated in FIG. 10F. The implant of FIG. 10F can be formed by making a mold of ridge 64 and using the mold to eventually produce an implant with an aperture 63 which will conform to ridge 64. Various techniques for making a mold of ridge 64 and using the mold to produce a duplicate of the ridge or to produce a shape which will conform to the ridge 64 are well known in the art and will not be discussed herein. After the implant of FIGS. 10F and 11 is slidably inserted on ridge 64 in the manner shown in FIG. 10F, malleable hydroxyapatite composition is pressed against and molded around against the implant and bone 52 and covered with a layer 24 which is secured to head 61 by head 21 of the healing cap illustrated in FIG. 1. The externally threaded end 20 of the healing cap is rotated into internally threaded aperture 67 formed in the upper end of head 61. If desired, an aperture(s) 68 can be formed through body 62 to permit a screw(s) to pass through the aperture 68 and into the bone 52 to secure the implant to the bone 52. In addition, a slot, indicated by dashed lines 66 in FIG. 10F, can be cut through ridge 64 to receive a panel 69 which is attached to arch 63 in the position indicated by dashed line 70.

Figure 12:
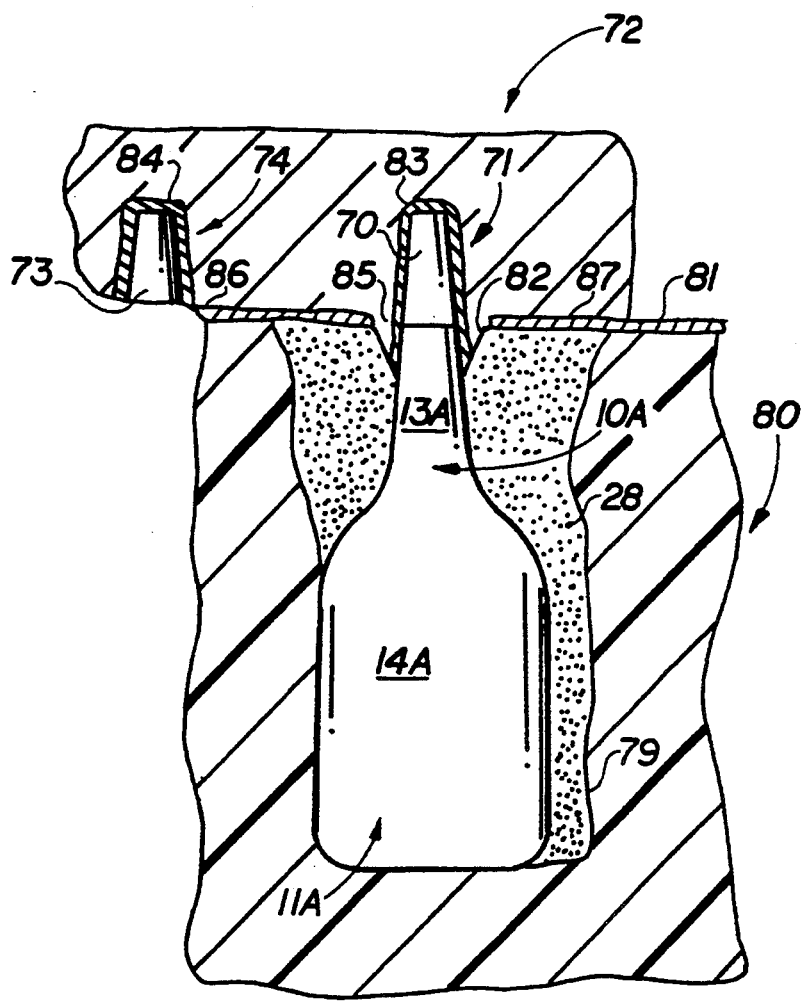
FIG. 12 is a side partial section view illustrating a molding procedure utilized in another embodiment of the invention.
Figure 13:
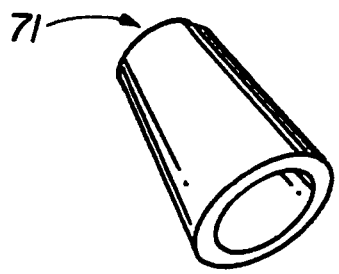
FIG. 13 is a perspective view of a sacrificial coping utilized in the embodiment of the invention illustrated in FIG. 12.

FIGS. 12 to 15 depict apparatus using in a molding method which is used in conjunction with the implant apparatus and methodology of the invention. In FIG. 12, an implant having a head 10A and bottom 11A is held in position in opening 79 formed in alveolar bone by a solidified hydroxyapatite composition 28. Composition 28 solidified when the surrounding alveolar bone 80 grew into the composition 28 in opening 79. Head 10A has a conical head which tapers upwardly from body 11A toward the gum tissue 81. Head 10A has outer smooth continuous surface 13A. Body 11A includes outer smooth continuous surface 14A. Frustoconical support member 70 is attached to head 10A. Sacrificial frustoconical coping 71 is slid over member 70. Sacrificial frustoconical coping 74 is slid over member 73. If desired, copings 71 and 74 can be metal and not be sacrificial. Member 73 is attached to the head 10A (not shown) of another implant (not shown) in the alveolar bone 80. Rubber, silicone, or some other acceptable material is used to form a negative mold 72 extending over and around copings 71 and 74 in the manner shown in FIG. 12. The use of such molding materials in dentistry is well known and will not be discussed herein. The negative mold includes upstanding hollow conical member 85; frustoconical hollows 83 and 84 which conform and adhere to copings 71 and 74, respectively; and, surfaces 86 and 87 which conform to gum tissue 81. When the negative mold 72 is removed from members 70 and 73, copings 71 and 74 are removed with and are imbedded in the mold 72.

Figure 14:
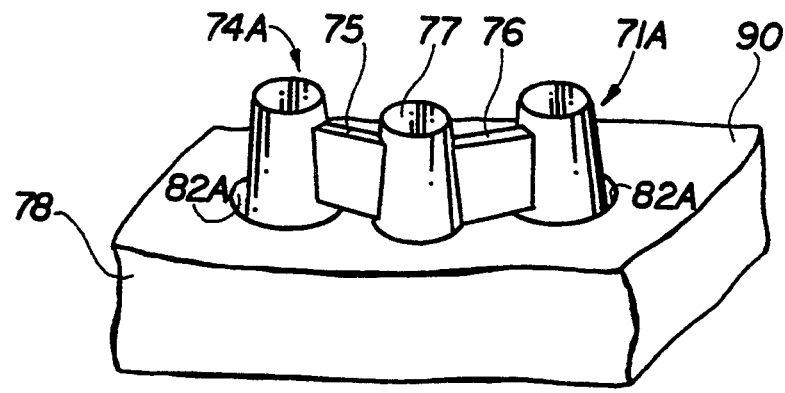
FIG. 14 is a perspective view illustrating another step in the molding procedure of FIG. 12.
Figure 15:
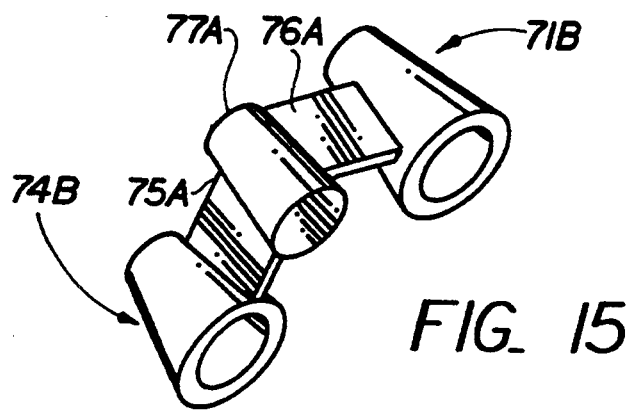
FIG. 15 is a perspective view illustrating a finished dental bridge produced according to the method of FIGS. 12 and 14; and, FIG. 16 is a side partial section view illustrating an artificial tooth removably attached to an implant apparatus.

After mold 72 has set and is removed from members 70 and 73 and from the patient's mouth, mold 72 is used to make a positive stone mold 78. This is, as is well known, accomplished by inverting mold 72, place mold 72 in a container which circumscribes mold 72, and by pouring a stone mold slurry into sacrificial copings 71 and 74 and over surfaces 86 and 87. After the stone mold slurry hardens to form mold 78, the mold 78 and mold 72 are heated until mold 72 melts and flows off of stone mold 78, or, mold 72 can simply be peeled oil of the hardened stone mold with or without copings 71 and 74. The positive stone mold 78 which remains replicates the gum line 81, support members 72 and 73, and the upper portion of each head 10A as shown in FIG. 12. The stone mold 78 also replicates 82A the conical groove or detent 82 formed around the upper portion of each implant head 10A. In FIG. 14, each conical groove 82 has a shape and dimension equal to the shape and dimension of conical groove 82 in FIG. 14. Also, in FIG. 14, the portions of the stone mold which replicate frustoconical members 70 and 73 are not visible because new sacrificial copings 71A and 74A have been slipped over said portions of the stone mold (or the copings 71 and 74 which were originally used in the mouth to make mold 72 can remain on said portions of the stone mold). While the shape and dimension of each coping can vary, in FIGS. 12 to 14, each coping 71, 74, 71A, 74A is of equivalent shape and dimension. The shape and dimension of each support member 70 and 73 can also vary as desired. In FIG. 12, however, each frustoconical support member 70 and 73 is of equal shape and dimension.

In FIG. 14 a pontic comprised of frustoconical support member 77 and ribs 75 and 76 has been constructed above the upper surface 90 of stone mold 78. The pontic interconnects sacrificial copings 71A and 74A and is positioned adjacent surface 90. The pontic is typically constructed from wax, but any other desired material can be utilized. Once the construction of the pontic is completed, the sacrificial bridge support of FIG. 14 is removed from mold 78 and mold 78 is discarded, or, mold 78 is retained for use in subsequent porcelain work. After the sacrificial bridge support is removed from mold 78, its shape and dimension and appearance is identical to that of the finished metal bridge support pictured in FIG. 15.

In the next step of the molding process, the sacrificial bridge support is submersed or "invested" in a stone mold slurry and, before or as the slurry hardens, a small escape channel is formed which leads from the sacrificial bridge support through and to the upper surface of the slurry. After the stone mold slurry hardens, it is heated to melt the wax pontic and the sacrificial copings 71A and 74A. The melted wax and melted materials from the copings 71A and 74A flows out of the stone mold through the escape channel. After all of the melted material flows out of the stone mold, a hollow exists in the stone mold which is a negative of the sacrificial support bridge of FIG. 14 and of the bridge of FIG. 15. The investment molding process is continued by pouring molten metal through the escape channel into this hollow and allowing the metal to harden. After the metal hardens, the finished support bridge of FIG. 15 has been formed in the stone mold. The stone mold is broken away from the bridge to free the finished bridge from the mold. Porcelain or another desired material is placed on the bridge supports 74B, 77A, and 71B to build artificial teeth on the bridge. Ordinarily, a single artificial tooth is built on each bridge support. After artificial teeth are constructed on the bridge supports, the bridge is inserted in the patient's mouth by placing hollow support 71B over member 70 and by placing hollow support 74B over member 73. Supports 74B and 71B can be glued or otherwise affixed to members 73 and 70, respectively.

Figure 16:
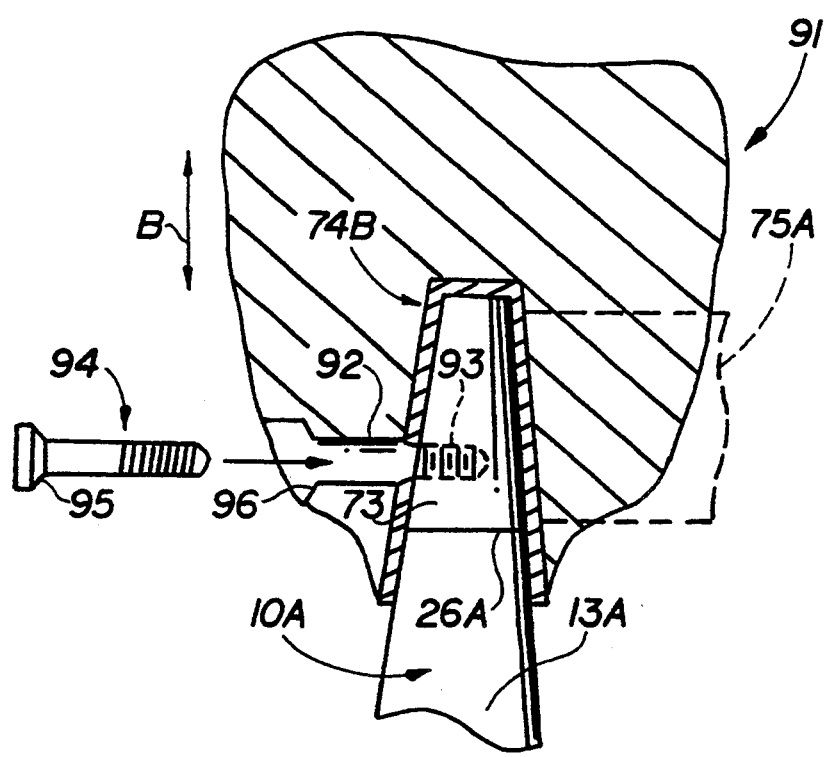

A method of removably attaching a bridge support 74B and artificial tooth 91 to a member 73 is illustrated in FIG. 16. In FIG. 16 a fastener 94 is inserted into aperture 92 and threaded into internally threaded aperture 93 in member 73. Precise alignment of apertures 92 and 93 is not required because the diameter of aperture 92 is slightly larger than that of aperture 93. The undersurface 95 of fastener conforms to and bears against a portion of conical surface 96 to prevent the tooth 91 from moving in the directions of arrows B. When fastener 94 is removed from apertures 92 and 93, coping 74B can be pulled upwardly off of and free from support member 73.

In FIG. 16, the upper distal end 26A of head 10A contacts the bottom of support member 73. The outer peripheral conical surface of head 10A is contiguous with and lies in a common conical plane with the outer conical surface 13A of head 10A. Coping 74B conforms to surface 13A and to the outer conical surface of member 73 so that coping 74B slidably engages and fits said conical surfaces in the manner illustrated in FIG. 16. The co-planar relationship of the conical surface of member 73 and the conical surface 13A of member 10A is important in the practice of the invention because it enables coping 74B and tooth 91 to extend sealingly downwardly below the gum line, i.e. to extend downwardly below end 26A.

Members 70 and 73 can be fabricated from metal or from plastic, rubber, copolymer, polymer, composites, or any other desired material, as can the sacrificial copings 71, 74, 71A, 74A.

The implant method and apparatus of the invention have several advantages. First, since the opening which is formed in the bone to receive the implant does not have to conform to the shape and dimension of the implant, special drills are not necessary when the opening is formed in the alveolar or basal bone to receive the implant. Second, drilling an opening in the bone which is larger than and does not conform to the shape and contour of the implant decreases the amount of heat generated during the drilling process. This is important because bone is damaged when exposed to heat in excess of 130 degrees centigrade for one minute or more. Conventional implants require that a cylindrical opening be drilled in the bone. Drilling such openings requires the use of internally irrigated slowly rotating burrs and is more likely to generate heat which damages the bone adjacent the cylindrical opening. When an opening is drilled for the implant of the invention, a higher speed externally irrigated burr can be utilized. Third, the implant of the invention permits non-resorbable hydroxyapatite to be utilized to fill in the opening around the implant. The non-resorbable hydroxyapatite produces a strong, tough structure which is less likely to have saucerization. Saucerization occurs when bone is lost from around the implant due to stress or bacterial invasion. This use of non-resorbable hydroxyapatite is particularly advantageous when a bone ridge which has receded is being augmented to duplicate the original shape and size of the ridge. Fourth, the lateral insertion of an implant in the manner illustrated in FIGS. 6 and 7 is useful in the case where a tooth has been missing for some time and adjacent teeth have migrated into and partially filled the space of the missing tooth. When this occurs, conventional implants either are forced to be so small that they are weak or are prevented from being utilized due to the small size of the space remaining between the adjacent teeth. The implant of FIGS. 1 and 8 solves this problem because it has a large base with a thin neck which can extend between the remaining adjacent teeth. Fifth, the implant method of the invention covers the junction between a support member 70 and the head 10A (FIG. 12) of the implant. In conventional implants, this junction is exposed to oral fluids and can corrode and fail. Further, dentists often do not screw or otherwise install member 70 snugly against the top of head 10A, leaving a septic gap. Sixth, the implant of FIGS. 1, 8 and 12 can be long or short and still provide a large outer surface area for anchoring the implant in the alveolar or basal bone.

Having described my invention in such terms as to enable those skilled in the art to understand and practice it, and having described the presently preferred embodiments thereof, I claim:

1. A method of anchoring a dental implant in the alveolar bone of a patient, comprising the steps of
    (a) forming an opening in the alveolar bone, said opening including a peripheral wall circumscribing and enclosing an open space;
    (b) inserting a dental implant in said opening, said dental implant comprising a body and a head supported on said body and adapted to support an artificial tooth, said dental implant only partially occupying said open space and being freely movable from side-to-side in said open space to contact and move away from said peripheral wall, a portion of said open space being unoccupied by said implant;
    (c) filling said portion of said open space with a bone inducing composition to fix said implant in a selected position in said opening, said composition hardening to form a structure which fixes said implant in position in said opening, said composition
        (i) extending from at least a portion of said wall to said implant and contacting said wall and said implant to fix said implant in position in said opening,
        (ii) extending from said bottom of said body upwardly over said body and said head of said implant, and
        (iii) facilitating the formation of new bone in said space an said opening which is filled with said composition;
    (d) waiting for said composition to harden; and,
    (e) waiting for bone to form in said space in said opening which is filled with said composition.

2. The method of claim 1 wherein
    (a) in step (c), said space in said opening which is unoccupied by said dental implant is filled with a porous composition which hardens into a structure which has pores and which permits the ingrowth of bone into said pores; and,
    step (e) comprises waiting for bone to form in said pores.

3. The method of claim 1 wherein
    (a) in step (c), said space in said opening which is unoccupied by said dental implant is filled with a composition which is resorbed by the body and promotes the formation of bone in said space in said opening which is unoccupied by said dental implant; and,
    (b) step (e) comprises waiting for said composition to be resorbed by the body and for bone to be formed in said space in said opening which is unoccupied by said dental implant.

4. The method of claim 1, wherein in step (c), said portion of said open space is completely filled with a resorbable bone inducing composition to fix said implant in a selected position in said opening, said composition hardening to form a structure which fixes said implant in position in said opening, said composition
    (i) extending from at least a portion of said wall to said implant and contacting said wall and said implant to fix said implant in position in said opening,
    (ii) extending from said bottom of said body upwardly over said body and said head of said implant, and,
    (iii) facilitating the formation of new bone in said space in said opening which is filled with said composition;
said unoccupied portion of said opening is filled with a bone inducing resorbable composition which hardens to maintain said implant in fixed position in said opening.

5. A method of anchoring a dental implant in the alveolar bone of a patient, comprising the steps of
    (a) forming an opening in the alveolar bone, said opening including a peripheral wall circumscribing and enclosing an open space;
    (b) inserting a dental implant in said opening, said dental implant comprising a body and a head supported on said body and adapted to support an artificial tooth, said dental implant only partially filling said open space and being freely movable in said opening, a portion of said open space being unoccupied by said implant;
(c) tilting and positioning said dental implant in said open space;
(d) filling said portion of said open space with a malleable composition to fix said implant in a selected position in said opening, said composition
  (i) subsequently hardening to form a structure which fixes said implant in position in said opening,
  (ii) extending from said wall to said implant and contacting said wall and said implant to fix said implant in position in said opening,
  (iii) extending from said bottom of said body upwardly over said body and said head of said implant, and
  (iv) facilitating the formation of new bone in said space in said opening which is filled with said malleable composition;
(e) waiting for said composition to harden; and,
(f) waiting for bone to form in said space in said opening which is filled with said hardened composition.

6. A method of anchoring a dental implant in the alveolar bone of a patient, comprising the steps of
(a) forming an opening in the alveolar bone, said opening including a peripheral wall circumscribing and enclosing an open space;
(b) inserting a dental implant in said opening, said dental implant comprising a body and a head supported on said body and adapted to support an artificial tooth, said dental implant only partially filling said open space and being freely movable in said opening, a portion of said open space being unoccupied by said implant;
(c) filling said portion of said open space with a malleable composition to fix said implant in a selected position in said opening, said composition
  (i) subsequently hardening to form a structure which fixes said implant in position in said opening,
  (ii) permitting said implant to be tilted to deform said malleable composition and reposition said implant,
  (iii) extending from said wall to said implant and contacting said wall and said implant to fix said implant in position in said opening,
  (iv) extending from said bottom of said body upwardly over said body and said head of said implant, and,
  (v) facilitating the formation of new bone in said portion of said open space which is filled with said malleable composition;
(d) tilting said implant to reposition said implant in said packed malleable composition;
(e) repacking said malleable composition; p1 (f) waiting for said composition to harden; and,
(g) waiting for bone to form in said space in said opening which is filled with said hardened composition.

* * * * *